United States Patent [19]
Katsushima et al.

[11] 3,956,405
[45] May 11, 1976

[54] PROCESS FOR MANUFACTURING POLYFLUOROALKYL PROPANOLS

[75] Inventors: Atsuo Katsushima, Takarazuka; Shinichi Imazu; Shoshin Fukui, both of Toyonaka; Akitoshi Iwatani, Suita; Tadashi Akazawa, Ibaragi, all of Japan

[73] Assignee: Daikin Kogyo Kabushiki Kaisha, Osaka, Japan

[22] Filed: Feb. 25, 1974

[21] Appl. No.: 445,324

[30] Foreign Application Priority Data
Feb. 27, 1973 Japan.............................. 48-23979

[52] U.S. Cl. ................................................. 260/633
[51] Int. Cl.² ........................................... C07C 31/34
[58] Field of Search ........................ 260/633, 632 B

[56] References Cited
UNITED STATES PATENTS
1,787,205  12/1930  Loehr .............................. 260/632 B FOREIGN PATENTS OR APPLICATIONS
320,424    10/1929  United Kingdom ............. 260/632 B
986,617     8/1961  United Kingdom ............. 260/632 B
970,790     9/1964  United Kingdom ............. 260/632 B
1,508,939  11/1967  France ............................. 260/632 B OTHER PUBLICATIONS
Park et al., J. Org. Chem. 26, (1961), 2089–2095.
Newman, J.A.C.S. 71, (1949), 3362–3363.

*Primary Examiner*—Howard T. Mars
*Attorney, Agent, or Firm*—Armstrong, Nikaido & Wegner

[57] ABSTRACT

In a catalytic reduction of polyfluoroalkylpropylene epoxide to produce a polyfluoroalkyl propanol, a process which is characterized in that said catalytic reduction is conducted in the presence of a weakly basic substance having a basic dissociation constant (pKb) at 25°C of at least 1.

6 Claims, No Drawings

PROCESS FOR MANUFACTURING POLYFLUOROALKYL PROPANOLS

This invention relates to a process for manufacturing a polyfluoroalkyl secondary propanol, more particularly to catalytic reduction of a polyfluoroalkylpropylene epoxide to produce a polyfluoroalkyl secondary propanol.

Polyfluoroalkyl propanols to be obtained by the present invention have been known as useful intermediates for producing water- and oil-repellent agents and surface active agents.

It has been known in the art to produce a polyfluoroalkyl propanol by reducing a polyfluoroalkylpropylene epoxide in an organic solvent by a reducing agent such as sodium boron hydride, lithium aluminum hydride or like complex metal hydrides. According to this method, however, the reaction necessitates a long period of time in order to obtain the desired product and further the yield of the product is poor in spite of the prolonged reaction time. Moreover, it is necessary to carry out the reaction in organic solvents in the absence of water, since undesired side reactions occur to produce byproducts due to hydrolysis of the starting epoxides, if water exists in the reaction system.

In order to overcome the drawbacks of the above known method the present inventors attempted to produce polyfluoroalkyl propanols by the catalytic reduction of polyfluoroalkylpropylene epoxides, but according to such attempt it has been found that the starting epoxides can not be converted to the desired propanols effectively even after a prolonged reaction time.

One object of the present invention is accordingly to provide a process for manufacturing polyfluoroalkyl propanols which overcomes the drawbacks of the known method.

Another object of the invention is to provide an improved process for manufacturing polyfluoroalkyl propanols by the catalytic reduction of polyfluoroalkylpropylene epoxides, whereby the desired polyfluoroalkyl propanols can be selectively obtained in a high yield within a short period of reaction time.

These and other objects and advantages of the present invention will be apparent from the following description.

In catalytic reduction of a polyfluoroalkylpropylene epoxide to produce a polyfluoroalkyl propanol, the present improved process is characterized in that said catalytic reduction is conducted in the presence of a weakly basic substance having a basic dissociation constant (pKb) at 25°C of at least 1.

According to the researches of the present inventors it has been discovered that when the catalytic reduction of polyfluoroalkylpropylene epoxides is conducted in the presence of a weakly basic substance, the reaction is markedly accelerated, thereby making it possible to obtain the desired polyfluoroalkyl propanols with a high conversion and selectivity within a short period of reaction time. In fact, it is possible in accordance with the present invention to prepare polyfluoroalkyl propanols with a conversion of not lower than 80% and a selectivity of not lower than 90% within not longer than 7 hours. Further, the reaction to produce the desired polyfluoroalkyl propanol proceeds effectively without undesired side reaction, i.e., hydrolysis of the starting polyfluoroalkylpropylene epoxide, even if water exists in the reaction system.

The polyfluoroalkylpropylene epoxides to be used in the invention are those having the formula of

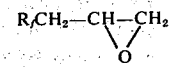

wherein $R_f$ is a polyfluoroalkyl group having 1 to 20, preferably 4 to 15, carbon atoms. The polyfluoroalkylpropylene epoxides are in the form of liquid or solid and can be prepared by various methods. For example, they can be easily obtained by dehydrogen iodide reaction in aqueous sodium hydroxide solution of a compound represented by the formula of $R_f$—$CH_2CHICH_2OH$, wherein $R_f$ is the same as defined before, which is prepared by reacting allyl alcohol with a polyfluoroalkyl iodide having the formula of $R_fI$, wherein $R_f$ is the same as defined before. The polyfluoroalkylpropylene epoxides thus produced can be used as the starting material of the invention in a crude form obtained merely by neutralizing excess alkali contained in the resulting reaction mixture with hydrochloric acid, sulfuric acid, carbonic acid or like acids without any complicated purification procedures, such as extraction, dehydration, etc. Preferable examples of the polyfluoroalkylpropylene epoxides are as follows:

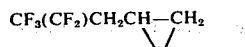

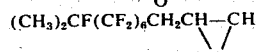

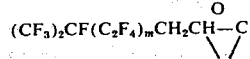 (a mixture of epoxides with m ranging from 1 to 8)

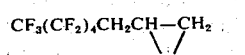

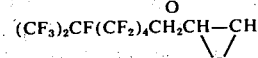

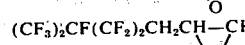

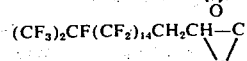

(a mixture of epoxides with m ranging from 1 to 20)

The catalysts to be used for the catalytic reduction of the invention are conventional catalysts heretofore used in catalytic reduction reactions, and include, for example, platinum, palladium and like platinum metals, reduced nickel, nickel oxide (NiO), Raney nickel and like nickel catalysts, copper-chromium oxide catalysts, etc. Of these catalysts preferable are palladium and Raney nickel. If necessary, the catalysts can be supported by inactive carriers, such as silicon carbide, magnesium sulfate, diatomaceous earth, pumice, active carbon, barium sulfate, calcium carbonate, asbestos, etc. The catalysts can be used alone or in admixture with one another, usually in an amount of 0.1 to 10 wt.%, preferably 0.2 to 3 wt.%, based on the weight of the starting polyfluoroalkylpropylene epoxide.

The weakly basic substances to be used in the invention include inorganic or organic weakly basic substances having a basic dissociation constant (pKb) at 25°C of at least 1. If the basic dissociation constant of the basic substance is less than 1, the reaction velocity can not be increased and further the desired propanols can not be obtained selectively with undesired side reactions. Preferable basic dissociation constant is in the range of 1.5 to 9.0, since the reaction velocity can not be increased sufficiently with basic substances having a basic dissociation constant of more than 9. Examples of the weakly basic substances to be used are (1) ammonia; (2) amines such as butyl amine, diethyl amine, trimethyl amine, triethyl amine and like lower alkyl amines, pyridine, melamine and like heterocyclic amines, aniline, benzyl amine and like aromatic amines, preferable being lower alkyl amines; (3) metal oxides such as CaO, MgO, etc.; and (4) salts of weak acids such as ammonium salts, alkali metal salts and alkaline earth metal salts of inorganic or organic weak acids having acidic dissociation constant (pKa) at 25°C of at least 1, preferably 1.5 to 9.0. Examples thereof are $CH_3COOK$, $C_2O_4K_2$, $HCOONa$, $C_6H_5COONa$, $C_6H_4(COONa)_2$, $(CH_3CH_2COO)_2Ca$ and like organic acid salts and $Na_2B_2O_7$, $K_3BO_3$, $NaHCO_3$, $Na_2CO_3$, $Na_2SO_3$, $(NH_4)_2HPO_4$, $Na_3PO_4$, $NaCN$ and like inorganic acid salts.

According to the present invention the weakly basic substance can be used as it is or in the form of aqueous solution. The amount thereof to be employed may vary over a wide range, but usually it is in the range of 20 to 300 mole %, preferably 110 to 150 mole %, based on the mole of the starting polyfluoroalkylpropylene epoxide.

According to one of the preferred embodiments of the present process the starting polyfluoroalkylpropylene epoxide, catalytic reducing catalyst and weakly basic substance are placed in a closed reactor, such as an autoclave. The weakly basic substance can be used as it is or in the form of aqueous solution. If necessary, organic solvents which have been employed in conventional catalytic reduction reactions can be added to the reaction system. Examples of the solvents to be used are methanol, ethanol, dioxane, ether, benzene, cyclohexane, etc. The reaction is carried out in a hydrogen gas stream. Preferably increased pressure is applied, although the reaction proceeds under atmospheric pressure. Preferable hydrogen pressure is in the range of 2 to 50 kg/cm². The reaction is advantageously conducted at room temperature, but it can be accelerated at an elevated temperature. Usually the reaction temperature is in the range of 10° to 70°C.

The desired polyfluoroalkyl propanol thus obtained can be separated from the resulting reaction mixture by distillation thereof after the catalyst used is filtered off.

For a better understanding of the invention examples are given below.

EXAMPLE 1

In a 500-ml stainless steel autoclave were placed 34.1 g of

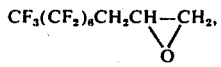

5 g of catalyst comprising active carbon impregnated with 5 wt.% of palladium, 12g of 23 wt.% ammonia water and 50 g of ethanol. To the autoclave hydrogen gas was introduced to a pressure of 30 kg/cm² and the mixture was reacted with stirring at 20°C for 4 hours. After the reaction the catalyst used was removed by filtration and washed with ethanol. The filtrate and the washings were combined and then distilled to obtain 30.2 g of a residue, i.e., $CF_3(CF_2)_6CH_2CH(CH_3)OH$ having a boiling point of 83°C/10 mm Hg.

Conversion: 96.2%. Selectivity: 92.1%.

EXAMPLE 2

In a 500-ml stainless steel autoclave were placed 34.1 g of

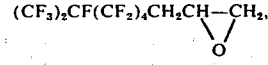

5 g of catalyst comprising calcium carbonate impregnated with 5 wt.% of palladium, 9.4 g of potassium acetate and 50 g of ethanol. To the autoclave hydrogen gas was introduced to a pressure of 10 kg/cm² and the mixture was reacted with stirring at 40°C for 5 hours. After the reaction the catalyst used was filtered off and washed with ethanol. The filtrate and the washings were combined and distilled to obtain 26.6 g of a residue, i.e., $(CF_3)_2CF(CF_2)_4CH_2CH(CH_3)OH$ having a boiling point of 88°C/13 mm Hg.

Conversion: 82.2%. Selectivity: 91.3%.

EXAMPLE 3

In a 500-ml stainless steel autoclave were placed 34.1 g of

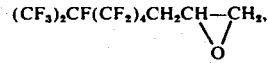

5 g of catalyst comprising calcium carbonate impregnated with 5 wt.% of palladium, 7 g of sodium bicarbonate and 20 g of water. The resulting mixture was reacted in the same manner as in Example 2, followed by the same separation procedures, whereby 26.8 g of $(CF_3)_2CF(CF_2)_4CH_2CH(CH_3)OH$ was obtained.

Conversion: 83.1%. Selectivity: 94.1%.

EXAMPLE 4

In a 500-ml autoclave were placed 40 g of

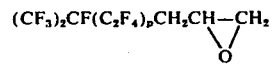

in the form of a mixture of epoxides with p ranging from 2 to 6, 3 g of Raney nickel, 10 g of triethylamine and 50 g of ethanol. To the autoclave hydrogen gas was introduced to a pressure of 30 kg/cm² and the mixture was reacted with stirring at 20°C for 4 hours. After the reaction the catalyst used was filtered off and washed with ethanol. The filtrate and the washings were combined and distilled to remove ethanol and triethylamine, whereby 39 g of $(CF_3)_2CF(C_2F_4)_pCH_2CH(CH_3)OH$ was obtained as a residue in the form of a mixture of alcohols with p ranging from 2 to 6.

Conversion: 96.4%. Selectivity: 92.0%.

EXAMPLE 5

Catalytic reduction was conducted in the same manner as in Example 4, except that 7 g of diethyl amine was used in place of 10 g of triethyl amine. The resulting product was separated from the reaction mixture in the same manner as in Example 4, whereby 34 g of $(CF_3)_2CF(C_2F_4)_pCH_2CH(CH_3)OH$ was obtained in the form of a mixture of alcohols with p ranging from 2 to 6.

COMPARISON

Catalytic reduction was carried out in the same manner as in Example 1, except that ammonia water was not used and the reaction was conducted at 40°C for 8 hours. The resulting $CF_3(CF_2)_6CH_2CH(CH_3)OH$ was separated from the reaction mixture in the same manner as in Example 1. The amount obtained was 4.8 g.

Conversion: 15.0%. Selectivity: 93.7%.

What we claim is:

1. In the process for producing a polyfluroalkyl secondary propanol by catalytically reducing with hydrogen a polyfluoroalkylpropylene oxide having the formula

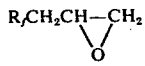

wherein $R_f$ is a polyfluoroalkyl group having 1–20 carbon atoms and the catalyst employed is selected from the group consisting of platinum, palladium, reduced nickel, nickel oxide, Raney nickel and copper-chronium oxide catalysts, the improvement comprising carrying out said reduction in the presence of an effective amount of a weakly basic substance having a basic dissociation constant (pKb) at 25°C. of at least 1 and at a temperature of 10° to 70°C.

2. The process of claim 1 wherein said process is carried out at a hydrogen pressure of 2 to 50 $Kg/_{cm}{}^2$.

3. The process according to claim 1, in which said polyfluoroalkyl group has 4 to 15 carbon atoms.

4. The process according to claim 1, in which said weakly basic substance has a basic dissociation constant (pKb) at 25°C of 1.5 to 9.

5. The process according to claim 1, in which said weakly basic substance is used in an amount of 20 to 300 mole %, based on the mole of the polyfluoroalkylpropylene epoxide.

6. The process according to claim 5, in which said amount of weakly basic substance is in the range of 110 to 150 mole %.

* * * * *